United States Patent [19]

Tietze et al.

[11] Patent Number: 5,126,437
[45] Date of Patent: Jun. 30, 1992

[54] ALDOPHOSPHAMIDE GLYCOSIDES, A PROCESS FOR THEIR PREPARATION AND THEIR USE AS PHARMACEUTICAL ACTIVE COMPOUNDS

[75] Inventors: Lutz-F. Tietze, Goettingen; Manfred Neumann, Marl; Roland Fischer, Goettingen, all of Fed. Rep. of Germany

[73] Assignee: Bayer Aktiengesellschaft, Leverkusen, Fed. Rep. of Germany

[21] Appl. No.: 362,902

[22] Filed: Jun. 7, 1989

[30] Foreign Application Priority Data

Jun. 9, 1988 [DE] Fed. Rep. of Germany ....... 3819634

[51] Int. Cl.⁵ .................. C07H 11/04; C07H 15/02; C07H 3/08; C07H 3/10
[52] U.S. Cl. ..................... 536/17.1; 536/4.1; 536/17.9; 536/18.4; 536/120
[58] Field of Search ............ 536/4.1, 17.1, 17.9, 536/18.4, 18.5, 120; 514/25; 424/464, 451

[56] References Cited

U.S. PATENT DOCUMENTS

| Re. 33,000 | 7/1989 | Gordon | 536/4.1 |
| 2,252,706 | 8/1941 | Coles et al. | 536/18.4 |
| 2,356,565 | 8/1944 | Chwala | 536/18.4 |
| 4,968,785 | 11/1990 | Moser et al. | 536/4.1 |

FOREIGN PATENT DOCUMENTS 0070444 1/1983 European Pat. Off.
0345583 12/1989 European Pat. Off.

OTHER PUBLICATIONS

Carbohydrate Research, vol. 164, 1987 pp. 177-194.
Liebigs Annalen Der Chemie, vol. 1987, 1987, pp. 847-856.
Carbohydrate Research, vol. 169, 1987, pp. 53-67.
Carbohydrate Research, vol. 180, 1988, pp. 253-262.
Liebigs Annalen Der Chemie, vol. 1990, Feb. 1990, pp. 151-157.
Tietze et al.; Carb. Res. 148:349-352 (1986).
Tietze et al.; Carb. Res. 164:177-194 (1987).
Tietze et al.; Carb. Res. 180:253-262 (1988).
Tietze et al.; Cancer Res. 49:4179-4184 (Aug. 1989).

*Primary Examiner*—Johnnie R. Brown
*Assistant Examiner*—Nancy S. Carson
*Attorney, Agent, or Firm*—Sprung Horn Kramer & Woods

[57] ABSTRACT

Compounds of the formula

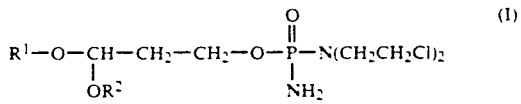

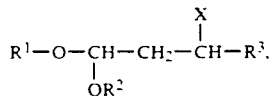

or

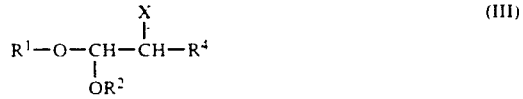

in which
- $R^1$ represents saturated, unsaturated or anhydro desoxypentosyl, desoxyhexosyl or didesoxyhexosyl, where the OH functions of the sugar are optionally protected, and
- $R^2$ represents straight-chain or branched or heterosubstituted alkyl having up to ten carbon atoms and
- $R^3$ represents straight-chain or branched or heterosubstituted alkyl having up to ten carbon atoms and
- X represents halogens and
- $R^4$ represents straight-chain or branched or heterosubstituted alkyl having up to ten carbon atoms.

Such compounds are useful as highly selective cytostatics in cancer therapy.

7 Claims, No Drawings

ALDOPHOSPHAMIDE GLYCOSIDES, A PROCESS FOR THEIR PREPARATION AND THEIR USE AS PHARMACEUTICAL ACTIVE COMPOUNDS

BACKGROUND OF THE INVENTION

1. Field of the Invention

The invention relates to new acid-labile acetal glycosides of aldophosphamide and other cytocidal aldehydes as acetal components, a process for their preparation and their use as highly selective cytostatics in cancer therapy.

2. Background Information

It is known that malignant cells show elevated glycolysis and lactate production compared to normal tissue and the pH in the tumor tissue can be lowered by intravenously administered glucose (compare S. Tanneberger, Experimentelle und klinische Tumorchemotherapie; Allgemeine Tumorchemotherapie (Experimental and Clinical Tumour Chemotherapy; General Tumour Chemotherapy); G. Fischer Verlag, Stuttgart/New York 1980; *Naturwiss.*, 46, 2 (1959); *Cancer Res.*, 42, 1498 (1982); 42, 1505 (1982)).

In the past, it has been attempted to use these differences in pH between normal and tumor tissue for selective tumor therapy (compare *Liebigs Ann. Chem.*, 1987, 847-856; *Tetrahedron Lett.*, 22 (1981) 239-242). It has been sought to convert alkylating compounds, which on account of too low a differentiation between healthy and malignant tissue, show a very low therapeutic breadth, into non-toxic, acid-labile prodrug forms which are only selectively cleaved in the tumor tissue to active, alkylating cytostatics for reasons of the low pH prevailing there. In this manner, it was intended to seek a selective tumor therapy.

However, it has been shown that the compounds prepared in the abovementioned references did not prove so acid-labile that they were selectively cleaved back to the active cytocidal agents in the tumor tissue.

SUMMARY OF THE INVENTION

It has now surprisingly been determined that the following mentioned compounds are non-toxic, while they can be converted by hydrolysis into cytocidal compounds at the pH attainable by hyperlycaemia in the tumour tissue.

The new compounds correspond to the general formulae (I), (II) and (III)

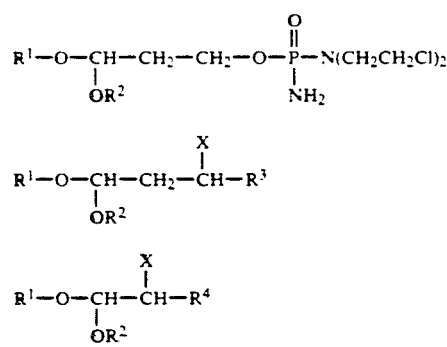

in which

R$^1$ represents saturated, unsaturated or anhydro desoxypentosyl, desoxyhexosyl or didesoxyhexosyl, where the OH functions of the sugar are optionally protected, and R$^2$ represents straight-chain or branched or heterosubstituted alkyl having up to ten carbon atoms and R$^3$ represents straight-chain or branched or heterosubstituted alkyl having up to ten carbon atoms and X represents halogens and R$^4$ represents straight-chain or branched or heterosubstituted alkyl having up to ten carbon atoms.

Preferred compounds of the general formulae (I), (II) and (III) are those in which R$^1$ represents saturated, unsaturated or anhydro-2-desoxyhexopyranosyl, 2,6-didesoxy-hexopyranosyl, 2-desoxy-pentofuranosyl, 2,3-didesoxy-hexenopyranosyl or 2,3-anhydropentofuranosyl, where the OH functions of the sugar are optionally protected, and R$^2$ represents straight-chain or branched alkyl having up to 6 carbon atoms and R$^3$ and R$^4$ represent hydrogen atoms.

Particularly preferred compounds of the general formulae (I), (II) and (III) are those in which R$^1$ represents 2-desoxy-α-D-arabino-hexo-pyranosyl, 2-desoxy-D-erythro-pento-pyranosyl, 2,6-didesoxy-α-L-arabino-hexo-pyranosyl, 2,3-anhydro-α-D-mannopyranosyl or 2,3-didesoxy-D-erythro-hex-2-enopyranosyl, where the OH functions of the sugar are optionally protected and R$^2$ represents straight-chain alkyl having up to 3 carbon atoms, R$^3$ and R$^4$ represent hydrogen atoms and X represents halogen.

Very particularly preferred compounds of the general formulae (I), (II) and (III) are those in which R$^1$ represents 2-desoxy-α-D-arabino-hexo-pyranosyl, 2,6-didesoxy-α-L-arabino-hexo-pyranosyl or 2,3-didesoxy-D-erythro-hex-2-eno-pyranosyl, where the OH functions of the sugar are optionally protected and R$^2$ represents methyl or ethyl, R$^3$ and R$^4$ represent hydrogen atoms and X represents halogen.

The customary protecting groups such as methylbenzoyl, benzoyl, acetyl or benzyl are suitable as OH-protecting groups. Benzyl, acetyl or methylbenzoyl are preferred. Acetyl (Ac) is particularly preferred.

In addition, a process for the preparation of the compounds of the general formula (I) according to the invention has been found, characterized in that, compounds of the general formula (IV)

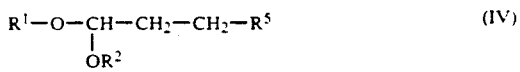

in which

R$^1$ and R$^2$ have the abovementioned meanings and

R$^5$ represents hydroxyl are reacted with N,N-bis(2-chloroethyl)-dichlorophosphoramide of the formula (V)

in the presence of bases, an ammonolysis is subsequently carried out and, if desired, the protective groups on the sugar residue are cleaved.

N,N-Bis-(2-chloroethyl)-dichlorophosphoramide of the formula (V) is known (compare *J. Am. Chem. Soc.*, 76, 655 (1954)).

Suitable diluents for the process are the customary inert organic solvents which do not change under the reaction conditions. These preferably include benzene, toluene, xylene, dichloromethane or dimethylformamide. Similarly, it is possible to use mixtures of the solvents mentioned. Benzene and dichloromethane are particularly preferably employed in the ratio 1:1.

Tert. amines may be used as bases. Triethylamine is particularly preferred.

The reaction proceeds in a temperature range from 20° C.-100° C., preferably at 40° C.

The process is carried out at atmospheric pressure.

The ammonolysis is preferably carried out at room temperature.

The compounds of the formula IV are new and may be obtained from the compounds of the formula (IVa)

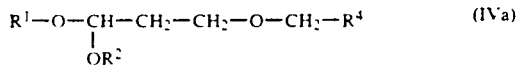

in which
R$^1$ and R$^2$ have the abovementioned meanings, and
R$^4$ represents phenyl or methoxyphenyl,
by debenzylation according to known methods (compare Reaktionen und Synthesen im organisch-chemischen Praktikum (Reactions and Syntheses in Practical Organic Chemistry), Thieme-Verlag, Stuttgart, New York 1981).

The compounds of the general formula (IVa) are new and can be obtained from the compounds of the formula (VI)

by reaction with acetals of the formula (VII)

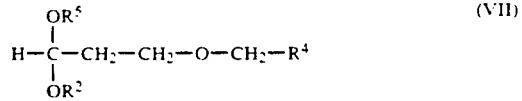

in which
R$^2$ and R$^4$ have the abovementioned meanings, and
R$^5$ represents methyl or ethyl
and with the aldehyde of the formula VIII

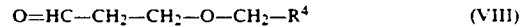

on which the compound V is based.

The compounds of the formula (VIII) can be prepared from the desoxycarbohydrates by known methods (compare *J. Org. Chem.*, 26, 908, 1961 and *Can. J. Chem.*, 56, 2889, 1978).

The acetals of the formula (VII) are known (compare *Heterocycles*, 15, 999 (1981); *Chem. Pharm. Bull.*, 15, 1893 (1967)).

3-Phenylmethoxypropionaldehyde is likewise known (compare *Synthesis*, 1981, 165).

DETAILED DESCRIPTION OF THE INVENTION

The compounds of the general formulae (I), (II) and (III) according to the invention show an unforseeable, useful spectrum of pharmacological activity.

The acid-labile glycosides of the inactivated cyclophosphamide of the general formula (I) for the first time represent a cytostatic which is non-toxic in its transport form. A cytocidal compound, the Friedman acid, is released by hydrolysis at the pH attainable in the tumour tissue by means of hyperglycaemia.

Cleavage experiments which were carried out according to working procedure 7 (GWP7) show that N,N-bis-(2-chloroethyl)-(3'RS)-1'-O-(3'-ethoxy-3'-(2,3-didesoxy-D-erythro-hex-2-enopyranosyloxy))-propyl-phosphoro-diamidate (Example 20) is preferably cleaved completely within 7 d at pH=5, up to 80% at pH=5.5 and up to 20% at pH=6.

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. In this connection, the therapeutically active compound should in each case be present in a concentration of about 0.5 to 90% by weight of the total mixture, i.e. in amounts which are sufficient in order to achieve the dosage range indicated.

The formulations are prepared, for example, by extending the active compound with solvents and/or excipients, optionally using emulsifiers and/or dispersants, where, for example, in the case of the use of water as a diluent, organic solvents may optionally be used as auxiliary solvents.

Auxiliary solvents which may be mentioned, for example, are: water, non-toxic organic solvents, such as paraffins, (for example, mineral oil fractions), vegetable oils (for example, groundnut/sesame oil), alcohols (for example, ethyl alcohol, glycerol), excipients, such as, for example, ground natural minerals (for example, kaolins, aluminas, talc, chalk), ground synthetic minerals (for example, highly disperse silica, silicates), sugars (for example, sucrose, lactose and dextrose), emulsifiers (for example, polyoxyethylene fatty acid esters, polyoxyethylene fatty alcohol ethers), dispersing agents (for example, ligninsulphite waste liquors, methylcellulose, starch and polyvinylpyrrolidone) and lubricants (for example, magnesium stearate, talc, stearic acid and sodium sulphate).

Administration takes place in a customary manner, preferably orally or parenterally, in particular perlingually or intravenously. In the case of oral administration, tablets may, of course, also contain additions, such as sodium citrate, calcium carbonate and dicalcium phosphate together with various additives, such as starch, preferably potato starch, gelatin and the like in addition to the excipients mentioned. Furthermore, lubricants, such as magnesium stearate, sodium lauryl sulphate and talc may additionally be used for tableting. In the case of aqueous suspensions, various flavor improvers or colourants may be added to the active compounds in addition to the abovementioned auxiliaries.

On oral administration, those galenical preparations are to be used in which the release of the active compound initially takes place in the intestine.

Release in the stomach may lead to an undesired premature acidolysis of the substances according to the invention.

In the case of parenteral use, solutions of the active compound may be employed using suitable liquid excipients.

In general, it has proved advantageous on intravenous administration to administer amounts of about 0.001 to 1 mg/kg, preferably about 0.01 to 0.5 mg/kg of body weight to obtain effective results, and on oral administration the dose is about 0.01 to 20 mg/kg, preferably 0.1 to 10 mg/kg of body weight.

In spite of this, it may be necessary to depart from the amounts mentioned, however, depending on the body weight or the type of administration, but also for reasons of the disorder and its individual behavior towards the medicament or the nature of its formulation and the point in time or interval at which administration takes place. Thus, in some cases it may be sufficient to manage with less than the previously mentioned minimum amount, whereas in other cases the upper limit mentioned must be exceeded. In the case of the administration of larger amounts, it may be advisable to divide these into a number of individual doses over the day.

EXPERIMENTAL PART

General working procedures

General working procedure 1 ("GWPI1") of the preparation of trimethylsilyl glycosides of the formula (VI) from the corresponding 1-hydroxy compounds 50.0 mmol of 1-hydroxy compound were dissolved in 50 ml of absolute pyridine and cooled under an argon atmosphere to 0° C. 7.0 ml of 1,1,1,3,3,3-hexamethyldisilazane (33.0 mmol) and then 2.2 ml of trimethylchlorosilane (17.0 mmol) were added dropwise to the solution, by means of which white pyridinium hydrochloride was precipitated. The conversion was monitored by thin layer chromatography. Working up was carried out by removing the pyridine at 40° C. on a rotary evaporator and taking up the white, oily residue in absolute ether. The suspension was filtered through a celite column, concentrated and, depending on the compound, chromatographed, distilled or crystallized.

General working procedure 2 ("GWP2") for the preparation of the acetal glycosides of the formula (IVa)

A solution of 1.00 mmol of trimethylsilyl glycoside of the formula (VI) was dissolved in 5 ml of absolute dichloromethane with the exclusion of moisture, and 1.00 mmol of acetal of the formula (VII) and 0.50 mmol of aldehyde of the formula (VIII) were added. The mixture was cooled under an argon atmosphere to −50° to −108° C., depending on the reactants. 18 μl of trimethylsilyl trifluoromethanesulphonate (0.10 mmol) were slowly added dropwise using a syringe. After completion of the reaction (TLC checking), 28 μl of triethylamine (0.20 mmol) were added and the reaction mixture was allowed to warm to 20° C. It was then filtered through a column of 2 g of silica gel (16–200 μm) using dichloromethane and the eluate was concentrated on a rotary evaporator. Purification and separation of diastereomers was carried out by chromatography on silica gel (32–63 μm).

General working procedure 3 (variant of working procedure 2) ("GWP3")

A solution of 1.00 mmol of trimethylsilyl glycoside of the formula (VI) was dissolved in 5 ml of absolute dichloromethane with the exclusion of moisture, and 1.50 mmol of acetal of the formula (VII) and 37 μl of acetone (0.50 mmol) were added. The reaction mixture was cooled under an argon atmosphere to −50° to −78° C., depending on the reactants. 18 μl of trimethylsilyl trifluoromethanesulphonate (0.10 mmol) were slowly added dropwise using a syringe. After completion of the reaction (TLC checking). 28 μl of triethylamine (0.20 mmol) were added and the reaction mixture was allowed to warm to 20° C. It was then filtered through a column of 2 g of silica gel (60–200 μm) using dichloromethane and the eluate was concentrated on a rotary evaporator. Purification and separation of diasteromers was carried out by chromatography on silica gel (32–63 μm).

General working procedure 4 (hydrogenolysis of the acetal glycoside benzyl ethers of the formula (IVa) to the alcohols of the formula (IV)) ("GWP4")

1.00 mmol of the benzyl compound of the formula (IVa) was dissolved in a mixture of 15 ml of ethyl acetate and 5 ml of ethanol.

212 mg of palladium on activated carbon (=0.20 mmol of Pd) and 106 mg of palladium on calcium carbonate (=0.10 mmol of Pd) were added and the mixture was shaken at 1 bar at room temperature under a hydrogen atmosphere. After complete conversion (TLC checking), catalyst was filtered off through a glass frit (P3), and the mixture was concentrated and chromatographed on silica gel.

General working procedure 5 (synthesis of the protected aldophosphamide glycosides of the formula (I)) ("GWP5")

1.00 mmol of the hydroxy compound of the formula (IV) was dissolved in 4 ml of a mixture of absolute benzene and absolute dichloromethane (1:1) with the exclusion of moisture. 558 μl of absolute triethylamine (4.00 mmol) were added using a syringe. 338 mg of N,N-bis(2-chloroethyl)dichlorophosphoric acid (V) (1.50 mmol) were added and the mixture was stirred at 40° C. After complete reaction of the educt (TLC checking), the mixture was evaporated to dryness on a rotary evaporator and taken up in 5 ml of absolute toluene. Dry ammonia gas was introduced slowly at room temperature. The course of the reaction was checked by thin layer chromatography and the toluene was removed in vacuo after completion. The residue was then chromatographed on silica gel.

General working procedure 6 (deblocking of the protected acetal glycosides of the formula (I)) ("GWP6")

60 mg of the compound of the formula (I) to be deprotected were dissolved in 1.5 ml of absolute methanol. 15 mg of $K_2CO_3$ were added. After 45 minutes, 1.5 ml of ether were added and the mixture was filtered through 5 g of silica gel (60–200 μm) (LS 8).

After removing the solvent, the compound was employed for the cleavage.

General working procedure 7 (acid cleavage of the acetal glycosides of the formula (I))

The compound to be cleaved was dissolved in 1 ml of water (double-distilled). 200 μl each were added to 1 ml of a buffer system which was thermostated at 37° C. Experiments were carried out at the following pH values: 5.0, 5.5, 6.0, 6.5 and 7.0. The cleavages were investigated after 1 hour, 2 hours, 4 hours, 8 hours and 24 hours and then at intervals of 24 hours by thin layer chromatography. The concentration of the phosphate buffer systems used was 0.05 mol/l.

General methods

Thin layer chromatography: prepared TLC plates SIL G/UV$_{254}$.

Mobile phase systems:

1) Ethyl acetate/petroleum ether (40-60): a) 1:1, b) 1:2, c) 2:1, d) 3:1
2) tert-Butyl methyl ethyl/petroleum ether (40-60) a) 1:1, b) 1:2, c) 1:3, d) 1:4, e) 2:3
3) Acetone/petroleum ether (40-60) a) 1:5, b) 3:2
4) Ether/petroleum ether (40-60) a) 1:1, b) 1:2, c) 1:5
5) Dicloromethane/methanol/petroleum ether (40-60) a) 10:1:1, b) 3:1:1
6) tert-Butyl methyl ether/dichloromethane/petroleum ether (40-60) 1:10:3
7) tert-Butyl methyl ether/dichloromethane 1:4
8) Diethyl ether/methanol 1:1

EXAMPLE 1

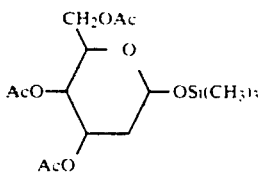

Synthesis of the educt: trimethylsilyl 3,4,6-tri-O-acetyl-2-desoxy-α-D-arabino-hexopyranoside 17.5 g of 3,4,6-tri-O-acetyl-2-desoxy-α-D-arabino-hexopyranose (60.3 mmol) were reacted according to GWP1. After completion of the reaction (15 minutes), the mixture was worked up and distilled in vacuo (bulb tube). B.p. 180° C./0.06 torr. 20 g (92%) of a colorless liquid which crystallized after a few hours were obtained.

m.p. 52° C., $[\alpha]_D^{20} = +102.8°$ (c=0.7, CHCl$_3$).
$R_F=0.60$ (LS 1a).

IR (KBr): 2980 (C—H), 1745 (C=O), 1365 (C—H), 1250, 1230 (C—O), 1045, 1005, 840 cm$^{-1}$ $^1$H-NMR (200 MHz, CDCl$_3$): δ=0.12 (s; 9H, Si(CH$_3$)$_3$), 1.79 (ddd, J$_{1,2a}$=3.0 Hz, J$_{2e,2a}$=12.5 Hz, J$_{2a,3}$=11.5 Hz, 1H, 2a-H), 2.05, 2.02, 1.99 (3xs; 9H, OAc), 2.12 (ddd, J$_{2e,1}$=1.5 Hz, J$_{2e,2a}$=12.5 Hz, J$_{2,3}$=5.5 Hz; 1H, 2-H$_e$), 3.99 (dd, J$_{6,6'}$=12.0 Hz, J$_{6,5}$=2.0 Hz; 1H, 6-H), 4.09 (ddd, J$_{5,6}$=2.0 Hz, J$_{5,6'}$=4.5 Hz, J$_{5,4}$=10.0 Hz; 1H, 5-H), 4.29 (dd, J$_{6',6}$=12.0 Hz, J$_{6',5}$=4.5 Hz; 1H, 6'-H), 4.97 (t, J$_{4,5}$=J$_{4,3}$=10.0 Hz; 1H, 4-H) 5.34 (dd, J$_{1,2e}$=1.5 Hz, J$_{1,2a}$=3.0 Hz; 1H, 1-H), 5.37 (dd, J$_{3,2e}$=5.5 Hz, J$_{3,2a}$=11.5 Hz; J$_{3,4}$=10 Hz; 1H, 3-H)

$^{13}$C-NMR (50.3 MHz, CDCl$_3$): δ−0.60 (SiMe$_3$), 20.29, 20.53 (OAc), 36.75 (C-2), 62.11 (C-6), 67.48, 68.55, 69.25 (C-3, C-4, C-5), 91.43

MS (70 eV): m/e=347 (3%, M$^+$—CH$_3$), 243 (7%), 229 (8%), 200 (16%), 185 (26%), 185 (26%), 161 (38%), 119 (76%), 117 (70%), 73 (47%, Si(CH$_3$)$_3$), 43 (100%, CH$_3$CO)

C$_{15}$H$_{26}$O$_8$Si (362.5) Calc.: C 49.71 H 7.23 Found: C 49.88 H 7.21

EXAMPLE 2

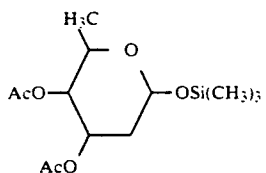

Trimethylsilyl-3,4-di-O-acetyl-2,6-didesoxy-α-L-arabino-hexopyranoside 4.20 g of 3,4-di-O-acetyl-2-desoxy-α,β-L-arabino-hexopyranoside (18.1 mmol) were reacted according to GWP1. After half an hour, the mixture was worked up and distilled in vacuo. B.p. 115° C./0.03 torr (bulb tube). 5.15 g (94%) of a colorless liquid were obtained. The anomer ratio was α:β=80:20. R$_F$=0.72 (LS 1a).
$[\alpha]_D^{20} = -134.5°$ (c=1, CHCl$_3$α-anomer).

IR (KBr): 2970 (C—H), 1740 (C=O), 1370 (C—H), 1250 (Si—O), 1230 (C—O), 1140, 1050 (C—O), 1010 (Si—O) 970, 890, 870, 850 (Si—C), 765 cm$^{-1}$ (Si—O)

$^1$H-NMR (200 MHz, CDCl$_3$): δ=0.12 (s; 9H, Si(CH$_3$)$_3$), 1.11 (d, J$_{6,5}$=6.5 Hz; 3H, 6-H$_3$), 1.75 (ddd, J$_{2a,1}$=3.5 Hz, J$_{2a,2e}$=13.0 Hz, J$_{2a,3}$=11.5 Hz; 1H, 2-H$_a$), 1.97, 2.02 (2xs; 6H, OAc), 2.10 (ddd, J$_{2e,1}$=1.5 Hz, J$_{2e,2a'}$=13.0 Hz, J$_{2,3}$=5.5 Hz; 1H, 2-H$_e$), 3.95 (dq, J$_{5,6}$=6.5 Hz, J$_{5,6}$=10.0 Hz; 1H, 5-H), 4.70 (t, J$_{4,3}$=J$_{4,5}$=9.5 Hz; 1H, 4-H), 5.25 (dd, J$_{1,2e}$=1.5 Hz, J$_{1,2a}$=3.5 Hz, 1H, 1-H), 5.32 (ddd, J$_{3,2e}$=5.5 Hz, J$_{3,2a}$=11.5 Hz, J$_{3,4}$=9.5 Hz; 1H, 3-H)

$^{13}$C-NMR (20 MHz, CDCl$_3$): δ=0.60 (Si(CH$_3$)$_3$), 17.11 (C-6), 20.36, 20.54 (OAc), 37.08 (C-2), 65.16, 68.61 (C-3, C-5), 74.73 (C-4), 91.22 (C-1), 169.58, 169.67 (C=O), MS (70 eV): m/e=289 (0,4%, M$^+$—CH$_3$), 229 (2, M—CH$_3$—HOAc), 172 (10%), 119 (16%), 78 (8%, Si(CH$_3$)$_3$), 43 (100%, CH$_3$CO)

C$_{13}$H$_{24}$O$_6$Si (304.4) Calc.: C 51.29 H 7.95 Found: C 51.46 H 7.99

EXAMPLE 3

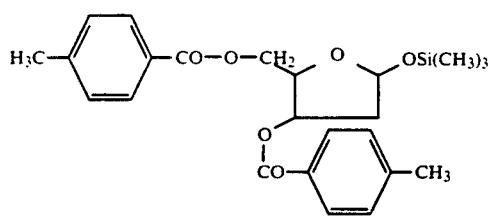

Trimethylsilyl-2-desoxy-3,5-di-O-(4-methylbenzoyl)-D-erythro-pentofuranoside

2-Desoxy-3,5-di-O-(4-methyl-benzoyl)-D-erythro-pentofuranoside (53.8 mmol) were reacted according to GWP1. Working up after 0.5 hours and chromatography on 140 g of silica gel (60-200 μm) (LS 4c) gave 19.3 g (81%) of a colorless oil. Separation of diastereomers by chromatography of 400 mg on 50 g of silica gel (LS 4c) gave 169 mg of the β-anomer.

R$_F$=0.37 (LS 4c) $[\alpha]^{20} = -3.2°$ (c=0.5, CHCl$_3$) and 150 mg of the α-anomer b R$_F$=0.27 (LS 4c) $[\alpha]_D^{20} = +81.4°$ (c=0.5, CHCl$_3$).

IR (Film): 3040 (C—H), 2980 (C—H), 1720 (C=O), 1620 (C=C), 1450, 1410, 1380 (C—H), 1280 C—O), 1180, 1110, 1025, 850, 760, 700 cm$^{-1}$ (C=C)

$^1$H-NMR (200 MHz, CDCl$_3$): α-anomer: δ=0.18 (s; 9H, Si(CH$_3$)$_3$), 2.19 (dd, J$_{2a,2e}$=14.5 Hz, J$_{2a,3}$=2.0 Hz; 1H, 2-H$_a$), 2.40, 2.42 (2xs; 6H CH$_3$), 2.49 (ddd, J$_{2e,1}$=5.0 Hz, J$_{2e,2a}$=14.5 Hz, J$_{2e,3}$=8.0 Hz; 1H, 2-H$_e$), 4.42–4.64 (m; 3H, 4-H, 5-H$_2$) 5.46 (ddd, J$_{3,2e}$=8.0 Hz, J$_{3,2a}$=2.0 Hz, J$_{3,4}$=3.0 Hz; 1H, 3-H), 5.72 (d, J$_{1,2a}$=5.0 Hz; 1H, 1-H), 7.20–7.30 (m; 4H, Ph—H), 7.88–8.00 (m; 4H, Ph—H) β-anomer: δ=0.14 (s; 9H, Si(CH$_3$)$_3$), 2.33 (dt, J$_{2a,1}$=5.0 Hz, J$_{2a,2e}$=14.0 Hz, J$_{2a,3}$=5.0 Hz; 1H, 2-H$_a$), 2.40, 2.42 (2xs; 6H, CH$_3$), 2.50 (ddd, J$_{2e,1}$=3.0 Hz, J$_{2e,2a}$=14.0 Hz, J$_{2e,3}$=7.0 Hz; 1H, 2-H$_e$), 4.50 (s(br); 3H, 4-H, 5-H$_2$), 5.60 (ddd, J$_{3,2e}$=7.0 Hz, J$_{3,2a}$=5.0 Hz, J$_{3,4}$=2.5 Hz; 1H, 3-H), 5.72 (dd, J$_{1,2e}$=3.0 Hz, J$_{1,2a}$=5.0 Hz; 1H, 1-H), 7.18–7.30 (m; 4H Ph—H), 7.90–8.04 (m; 4H, Ph—H)

$^{13}$C-NMR (20 MHz, CDCl$_3$): α-anomer: δ=−0.02 (Si(CH$_3$)$_3$), 21.41 (CH$_3$), 41.28 (C-2), 64.35 (C-6), 74.88, 81.35 (C-3, C-4), 98.79 (C-1), 126.98, 127.10, 128.88, 129.48, 129.56, 143.47, 143.60 (C-arom.), 165.98, 166.10 (C=O)

β-anomer: δ=−1.63 (Si(CH$_3$)$_3$), 19.87 (CH$_3$, 39.85 (C-2), 63.67 (C-6), 74.14, 79.88 (C-3, C-4), 97.61 (C-1), 125.25, 125.49, 127.28, 127.34, 127.96, 128.07, 141.84, 142.16 (C-arom.), 164.28, 164.52 (C=O) MS (70 eV): m/e=427 (1%, M$^+$—CH$_3$), 306 (11%, M—CH$_3$C$_6$H$_4$CO$_2$H), 293 (11%), 216 (8%), 209 (9%), 193 (10%), 157 (22%), 119 (100%, COC$_6$H$_4$CH$_3$) 91 (19%, CH$_3$C$_6$H$_4$), 73 (21%, Si(CH$_3$)$_3$)

C$_{24}$H$_{30}$O$_6$Si (442.6) Calc.: C 65.13 H 6.83 Found: C 65.24 H 6.99

EXAMPLE 4

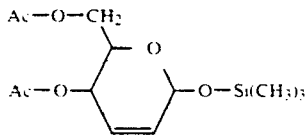

Trimethylsilyl 4,6-di-O-acetyl-2,3-di-desoxy-D-erythro-hex-2-enopyranoside 5.00 g of 3,4,6-tri-O-acetyl-1,5-anhydro-2-desoxy-D-arabino-hex-1-enitol (18.4 mmol) were added rapidly with stirring to 100 ml of boiling water and heated further under reflux. After 14 minutes, the solution was brought to room temperature as rapidly as possible with the aid of an ice bath. 1.8 g of BaCO$_3$ were slowly added. The mixture was then extracted 5 times using 30 ml of dichloromethane and the organic phase was dried with Na$_2$SO$_4$. The solution was added to a Pyrex glass photoreactor and irradiated for 1 h at −20° C. with a 500 watt lamp. Removing the solvent and chromatography on 2 times 230 g of silica gel (LS 1a) gave 3.26 g of a colorless oil which was still slightly contaminated by dimeric by-products. R$_F$=0.38 (LS 1a), R$_F$=0.40 (LS 1a, dimer). The product was further reacted according to GWP1. After 0.5 hours, the mixture was worked up and distilled in vacuo. B.p. 125° C./0.05 torr. 3.31 g (60%) of a colorless oil were obtained.

R$_F$=0.41 (LS 2e) [α]$_D^{20}$=+99.3° (c=1, CHCl$_3$).
Diastereomer ratio α:β=I:II=4:1

IR (Film): 3040 (C=C), 2960, 2900 (C—H), 1740 (C=O), 1370 (C—H), 1250 (C—O), 1110, 1040 (Si—O), 980, 890, 850 cm$^{-1}$ (C=C)

$^1$H-NMR (200 MHz, CDCl$_3$): δ=0.13 (S, 1.8H, Si(CH$_3$)$_3$, II), 0.14 (s; 7.2H, Si(CH$_3$)$_3$, I), 2.04, 2.06, (2xs; 6H, OAc), 4.06–4.24 (m; 3H, 6-H$_2$), 5-H), 5.10–5.42 (m, 2H, 1-H, 4-H), 5.80 (s; 1.6H, 2-H, 3-H, I), 5.84 (s; 0.4H, 2-H, 3H, II), $^{13}$C-NMR (50.3 MHz, CDCl$_3$): δ=−0.3 (Si(CH$_3$)$_3$, I), 0.00 (Si(CH$_3$)$_3$, II), 20.38, 20.56 (OAc), 62.82, 66.52 (C-4, C-5, I), 88.61 (C-1, I), 90.98 (C-1, II), 125.66, 132.52 (C-2, C-3, II), 127.02, 129.82 (C-2, C-3, I), 169.74, 170.20 (C=O)

MS (70 eV): m/e=287 (0.6% M$^+$—CH$_3$), (8%, M—CH$_3$CO$_2$), 229 (1%, M-aglycone), 200 (34%, AcO(CH)$_4$OSi(CH$_3$)$_3$), 158 (100%, HO(CH)$_4$OSi(CH$_3$)$_3$, 117 (65%), 73 (66%, Si(CH$_3$)$_3$), 43 (100%, CH$_3$CO)

C$_{13}$H$_{22}$O$_6$Si (302.4) Calc.: C 51.63 H 7.33 Found: C 51.78 H 7.46

EXAMPLE 5

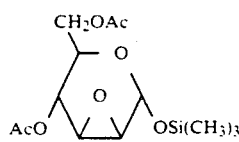

Trimethylsilyl-4,6-di-O-acetyl-2,3-anhydro-α-D-mannopyranoside 2.18 g of 4,6-di-O-acetyl-2,3-anhydro-α-D-mannopyranose (8.85 mmol) were reacted according to GWP1. After 0.5 hours, the mixture was worked up and the residual pyridine was removed overnight at room temperature in an oil pump vacuum. Crystallization from pentane gave 2.46 g (89%) of product. M.p. 60° C., R$_F$=0.45 (LS 1a) [α]$^{20}$=+62.5° (c=1 CHCl$_3$).

IR (Film): 3020, 2970, 2920 (C—H), 1750 (C=O), 1370 (C—H), 1260, 1230 (C—O), 1140, 1070, 1040, 890, 850 cm$^{-1}$ $^1$H-NMR (200 MHz, CDCl$_3$): δ=0.18 (s; 9H, Si(CH$_3$)$_3$, 2.24, 2.31 (2xs; 6H, OAc), 3.01 (dd, J$_{3,2}$=3.5 Hz, J$_{3,4}$=1.0 Hz; 1H, 3-H), 3.20 (d, J$_{2,3}$=4.5 Hz, 1H 2-H), 3.88–3.98 (mc; 1H, 5-H), 4.04–4.10 (m; 2H, 6-H$_2$), 4.84 (dd, J$_{4,3}$=1.0 Hz, J$_{4,5}$=10.0 Hz; 1H, 4-H), 5.32 (s; 1H, 1-H)

$^{13}$C-NMR (50 MHz, CDCl$_3$): δ=−0.26 (Si(CH$_3$)$_3$), 20.58, 20.67 (OAc), 50.45, 52.96 (C-2, C-3), 62.85, 64.26 (C-4, C-5), 63.00 (C-6), 89.50 (C-1), 169.28, 170.38 (C=O)

MS (70 eV): m/e=303 (10%, M$^+$—CH$_3$), 258 (2%, M—HOAc), 216 (10%, M—HOAc-ketene), 174 (33%, HOCCHCHOCH$_2$OSiMe$_3$), 117 (65%), 98 (91%), 74 (66%, Si(CH$_3$)$_3$), 43 (100%, CH$_3$CO)

C$_{13}$H$_{22}$O$_7$Si (318.4) Calc.: C 49.05 H 6.96 Found: C 49.31 H 7.13

EXAMPLE 6

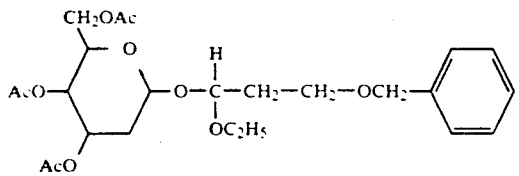

(1'RS)-1'-Ethoxy-3'-phenylmethoxy-propyl-3,4,6-tri-O-acetyl-2-desoxy-α-D-arabino-hexopyranoside 500 mg of the compound produced by Example 1 (1.38 mmol) were reacted at −70° with 3-phenylmethoxypropionaldehyde diethyl acetal (A) and 3-phenylmethoxypropionaldehyde according to GWP2. After 24 hours, half the amount of trimethylsilyl trifluoromethanesulphonate, A and 3-phenylmethoxypropionaldehyde are added once more.

After 48 hours, the reaction was discontinued and worked up, and the product was chromatographed on 80 g of silica gel (LS 2b). 579 mg (87%) of a colorless oil were obtained. $R_F = 0.17$ (LS 3a).

$[\alpha]_D^{20} = +84.7°$ (c=1, CHCl₃). Diastereomer ratio: (1R,1'R):(1R,1'S)=I:II=80:20.

IR (Film): 2990 (C—H), 1740 (C=O), 1370 (C—H), 1230 (C—O), 1140, 1100, 1040, 980, 740, 700 cm⁻¹

¹H-NMR (200 MHz, CDCl₃): δ 1.16 (t, $J_{2'',1''}=7.0$ Hz; 0.75H, 1''-H, II), 1.18 (t, $J_{2'',1''}=7.0$ Hz; 2.25H, 1''-H, I), 1.87 (ddd, $J_{2a,1}=4.0$ Hz, $J_{2a,2e}=13.0$ Hz, $J_{2a,3}=11.5$ Hz; 1H, 2-$H_a$) 1.92-2.10 (m; 2H, 2'-H₂), 2.02, 2.04 (2xs; 9H, OAc), 2.36 (ddd, $J_{2e,1}=1.5$ Hz, $J_{2e,2a}=13.0$ Hz, $J_{2e,3}=5.5$ Hz; 1H, 2-$H_e$), 3.44-3.86 (m; 4H, 3'H₂, 1''-H₂), 3.92-4.16 (m; 2H, 6-H, 5-H), 4.24 (dd, $J_{6,6'}=12.5$ Hz, $J_{6,5}=5.0$ Hz; 0.75 H, 6'-H, I), 4.24-4.34 (m; 0.25H, 6'-H, II), 4.50 (s(br); 2H, CH₂-phenyl), 4.84 (t, $J_{1',2'}=6.0$ Hz; 0.25H, 1'-H, II) 4.92 (t, $J_{1',2'}=6.0$ Hz; 0.75H, 1'-H, I), 5.00 (t, $J_{4,3}=J_{4,5}=9.5$ Hz; 0.75H, 4-H, I), 5.01 (t, $J_{4,3}=J_{4,5}=9.5$ Hz; 0.25H, 4-H, II), 5.22 (dd, $J_{1,2e}=1.5$ Hz, $J_{1,2a}=4.0$ Hz; 0.25H, 1-H, II), 5.31 (dd, $J_{1,2e}=1.5$ Hz, $J_{1,2a}=4.0$ Hz; 0.75H, 1-H, I), 5.34 (ddd, $J_{3,2e}=5.5$ Hz; $J_{3,2a}=11.5$ Hz, $J_{3,4}=9.5$ Hz; 1H, 3-H), 7.36 (s(br); 5H, phenyl-H)

¹³C-NMR (50.3 MHz, CDCl₃): δ=15.20 (C-2'', II), 15.33 (C-2'', I), 20.65, 20.71, 20.96 (OAc), 34.70, 34.83 (C-2, C-2', I), 35.27, 35.51 (c-2, C-2', II), 62.27 (C-1'', I), 62.45 (C-6), 63.74 (C-1'', II), 65.96 (C-3', II), 66.13 (C-3', I), 68.28, 69.03, 69.33 (C-3, C-4, C-5, I), 68.42, 69.20 (C-3, C-4, C-5, II), 73.00 (Phenyl-CH₂—O), 92.98 (C-1, I) 93.80 (C-1, II) 97.86 (C-1', I), 101.77 (C-1', II), 127.54, 127.60, 127.73, 128.35 (C-2, C-3, C-5, arom.), 138.25 (C-1, arom.), 169.82, 170.11, 170.19 (C=O)

MS (70 eV): m/e=274 (1%, M+H⁺-Aglycon), 273 (8%, M-aglycone, 214 (4%, M+H-aglycone 213 (33%, M-aglycone HOAc), 193 (21%, CH(OC₂H₅)(CH₂-)₂—O—CH₂-phenyl), 153 (26%, M-aglycone-2xHOAc), 111 (M-aglycone2xHOAc-ketene, 91 (96%, CH₂—C₆H₅), 87 (51%), 86 (96%), 43 (100%, CH₃CO).

C₂₄H₃₄O₁₀ (482.5) Calc.: C 59.74 H 7.10 Found: C 59.90 H 7.22

EXAMPLE 7

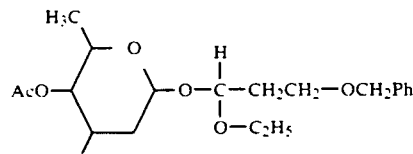

(1'RS)-1'-Ethoxy-3'-phenylmethoxy-propyl-3,4-di-O-acetyl-2,6-di-desoxy-α-L-arabino-hexopyranoside 400 mg of trimethylsilyl 3,4-di-O-acetyl-2,6-didesoxy-α-L-arabino-hexopyranoside (Example 2) (1.31 mmol) were reacted at −78° C. with 3-phenylmethoxypropionaldehyde diethyl acetal and 3-phenylmethoxypropanal according to GWP2. After 24 hours, half the amount of trimethylsilyl trifluoromethanesulphonate, 3-phenylmethoxypropionaldehyde diethyl acetal and 3-phenylmethoxypropanal were added. After 48 hours, the reaction was worked up and the product was chromatographed on 80 g of silica gel (LS 2c). 517 mg (93%) of a colorless oil were obtained.

$R_F = 0.33$ (LS 2e). $[\alpha]_D^{20} = -112.0°$ (c=1, CHCl₃). Diastereomer ratio (1S,1'S):(1S:1'R)=I:II 75:25.

IR (Film): 3040 (C—H), 2980, 2940 (C—H), 2880 (C—H), 1750 (C=O), 1370 (C—H), 1250, 1240 (C—O), 1140, 1050, 980, 740+705 cm⁻¹ (C—C, arom. monosubst.)

¹H-NMR (200 MHz, CDCl₃): δ=1.10 (d, $J_{6,5}=6.0$ Hz; 0.75H, 6-H₃, I), 1.12 (d, $J_{6,5}=6.0$ Hz; 0.25H, 6-H₃, II), 1.17 (t, $J_{2'',1''}=7.0$ Hz; 0.75H, 2''-Hg II), 1.18 (t, $J_{2'',1''}=7.0$ Hz; 2.25H, 2''-H₃, I), 1.82 (ddd, $J_{2a,1}=4.0$ Hz $J_{2a,2e}=13.0$ Hz, $J_{2a,3}=11.5$ Hz; 1H, 2-$H_a$), 1.90-2.03 (m; 2H, 2'-H₂), 2.01, 2.04 (2xs; 6H, OAc), 2.23 (ddd, $J_{2e,1}=1.5$ Hz, $J_{2e,2a}=13.0$ Hz, $J_{2e,3}=5.5$ Hz; 1H, 2-$H_e$), 3.40-3.77 (m; 2H, 1''-H₂), 3.59 (t, $J_{3',2'}=6.0$ Hz; 2H, 3'-H₂) 3.86 (dq, $J_{5,6}=6.5$ Hz, $J_{5,4}=9.5$ Hz; 0.75H, 5-H, I) 4.01 (dq, $J_{5,6}=6.5$ Hz, $J_{5,4}=9.5$ Hz; 0.25H, 5-H, II), 4.41-4.57 (m; 2H, CH₂—C₆H₅), 4.73 (t, $J_{4,5}=J_{4,3}=9.5$ Hz; 1H, 4-H), 4.80 (t, $J_{1',2'}=5.5$ Hz; 0.25H, 1'-H, II), 4.91 (t, $J_{1',2'}=6.0$ Hz; 0.75H, 1'-H, I), 5.09 (dd, $J_{1,2e}=1.5$ Hz, $J_{1,2a}=4.0$ Hz; 0.25H, 1-H, II), 5.21 (dd, $J_{1,2e}=1,5$ Hz, $J_{1,2a}=4.0$ Hz, 0.75H, 1-H, I), 5.28 (ddd, $J_{3,2e}=5.5$ Hz, $J_{3,2a}=11.5$ Hz, $J_{3,4}=9.5$ Hz; 1H, 3-H), 7.20-7.40 (m, 5H, phenyl—H).

¹³C-NMR (50.3 MHz, CDCl₃): δ=15.18 (C-2'', II), 15.33 (C-2'', I), 17.51 (C-6), 20.74, 20.93 (OAc), 34.68, 35.10 (C-2, C-2', I), 35.29, 35.74 (C-2, C-2', II), 62.08 (C-1'', I), 63.42 (C-1'', II), 65.95 (C-3', II), 66.17 (C-3', I); 66.02, 68.95 (C-3, C-5, I), 66.08, 69.01 (C-3, C-5, II), 72.87 (O—CH₂—C₆H₅), I), 72.92 (O—CH₂—C₆H₅, II), 74.72 (C-4), 92.72 (C-1, I), 93.76 (C-1, II), 97.44 (C-1', I), 101.51 (C-1', II), 127.37, 127.45, 127.59, 128.18 (C-2, C-3, C-4, arom.), 136-17, 136.23 (C-1, arom.), 169.83, 169.90 (C=O)

MS (200 eV, DCl, NH₃): m/e=442 (100%, M+NH₄⁺)

C₂₂H₃₂O₈ (424,5) Calc C 62.25 H 7.60 Found C 62.33 H 7.55

EXAMPLE 8

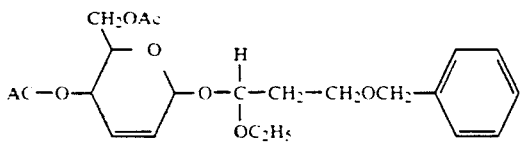

(1'RS)-1'-Ethoxy-3'-phenyl-methoxy-propyl-4,6-di-O-acetyl-2,3-di-desoxy-D-erythro-hex-2-enopyranoside 300 mg of the compound from Example 4 (1.02 mmol) were reacted at −90° C. with phenylmethoxypropionaldehyde diethyl acetal and 3-phenylmethoxypropanal according to GWP2. After 24 hours, the mixture was worked up and the product was chromatographed on 70 g of silica gel (LS 6). 281 g (65%) of a colorless oil were obtained. $R_F$=0.53 (LS 1a) $[\alpha]_D^{20}$=+94.7° (c=1, CHCl$_3$). The product mixture consisted of 2 diastereomers of α-configuration in the ratio (1R,1'R):(1R,1'S)=I:II=66:34.

IR (Film): 3050 (C—H), 3020 (C=C), 2980, 2930 (C—H), 2870 (C—H), 1740 (C=O) 1370 (C—H), 1240 (C—O), 1100, 1030, 970, 740, 700 cm$^{-1}$ $^1$H-NMR (200 MHz, CDCl$_3$): δ=1.19 (t, J$_{2'',1''}$=7.0 Hz; 3H, 2''-H$_3$), 1.90-2.08 (m; 2H, 2'-H$_2$, 2.04, 2.09 (2xs; 6H, OAc), 3.42-3.56 (m; 1H, 1''-H), 3.56 (t, J$_{3',2'}$=6.0 Hz; 1.32H, 3'-H$_2$, I), 3.58 (t, J$_{3',2}$=6.0 Hz; 0.66H, 3'-H$_2$, II), 3.70 (dq, J$_{1'',2''}$=7.0 Hz, J$_{1''',1''}$=9.5 Hz; 0.66H, 1'''-H, I), 3.82 (dq, J$_{1''',1''}$=9.5 Hz; 0.33H, 1'''-H, II), 4.02-4.32 (m; 3H, 6-H$_2$, 5-H), 4.48 (A-part of the AB-system, J=12.0 Hz; 1H, CH$_2$—C$_6$H$_5$), 4.51 (B-part of the AB-system, J=12.0 Hz; 1H, CH$_2$—C$_6$H$_5$), 4.91 (t, J$_{1',2}$=6.0 Hz; 0.33H, 1'H, II), 5.00 (t, J$_{1',2}$=5.5 Hz; 0.66H, 1'-H, I), 5.24-5.38 (m; 2H, 1-H, 4-H), 5.66-6.00 (m; 2H, 2-H, 3-H), 7.34 (s(br)); 5H, C$_6$H$_5$)

$^{13}$C-NMR (20 MHz, CDCl$_3$): δ=15.16 (C-2'', II), 15.32 (C-2'', I), 20.50, 20.59, 20.78 (OAc), 35.22 (C-2', I), 35.52 (C-2', II), 62.31, 62.98, 63.13, 63.38 (C-1'', C-6), 65.07, 67.41 (C-4, C-5, II), 65.26, 67.25 (C-4, C-5, I), 66.02 (C-3', II), 66.15 (C-3', I) 72.92 (OCH$_2$—C$_6$H$_5$), 90.40 (C-1, II), 91.14 (C-1, I), 99.39 (C-1', I), 101.32 (C-1', II), 127.50, 127.59, 127.64, 127.79, 128.14, 128.29, 128.71, 129.12 (C-2, C-3, C-4 arom., C-2, C-3), 138.44 (C-1 arom.), 169.92, 170.32, 170.37 (C=O)

MS (70 eV): m/e=213 (21%, M$^+$-aglycone), 163 (31%), 153 (17%, M-Aglycon-HOAc), 111 (39% M-aglycone) ketene), 91 (83%, CH$_2$—C$_6$H$_5$), 86 (52%, C$_2$H$_5$O—CH—CH$_2$—CH$_2$), 43 (100%, CH$_3$CO)

C$_{22}$H$_{30}$O$_8$ (422.5) Calc.: C 62.55 H 7.15 Found: C 62.42 H 7.14

EXAMPLE 9

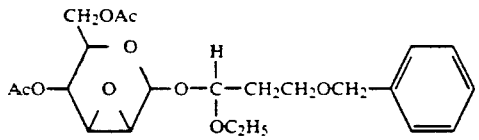

(1'RS)-1'-Ethoxy-3'-phenylmethoxy-propyl-4,6-di-O-acetyl-2,3-anhydro-α-D-mannopyranoside 141 mg of the compound from Example 5 (0.44 mmol) were reacted at −70° C. with 3-phenylmethoxypropionaldehyde diethyl acetal and 3-phenylmethoxypropional according to GWP2. After 24 hours, the mixture was worked up and the product was chromatographed on 20 g of silica gel (LS 2b). 100 mg (51%) of a colorless oil were obtained. $R_F$=0.29 (LS 2e) $[\alpha]_D^{20}$=−67.8° (c=1, CHCl$_3$).

Diastereomer ratio (1R,1'R):(1R,1'S)=I:II=60:40.

IR (Film): 2980, 2940 (C—H), 2870 (C—H), 1750 (C=O), 1370 (C—H), 1240 (C—O), 1140, 1100, 1040, 970, 740, 700 cm$^{-1}$ (C=C)

$^1$H-NMR (200 MHz, CDCl$_3$): 1 Diastereomer: δ=1.21 (t, J$_{2'',1''}$=7.0 Hz; 3H, 2''-H$_3$), 1.93-2.09 (m; 2H, 2'-H$_2$), 2.00, 2.12 (2xs; 6H, OAc), 3.13 (dd, J$_{3,2}$=3.5 Hz, J$_{3,4}$=1.0 Hz; 1H, 3-H), 3.24 (d, J$_{2,3}$=3.5 Hz; 1H, 2-H), 3.47-3.64 (m; 3H, 1''-H, 3'-H$_2$), 3.73 (dq, J$_{1''',2''}$=7.0 Hz, J$_{1''',1''}$=9.5 Hz; 1H, 1'''-H), 3.83-3.94 (mc; 1H, 5-H), 4.03-4.14 (m; 2H, 6-H$_2$), 4.47 (A-part of the AB-system, J=12.0 Hz; 1H, CH$_2$-Ph), 4.51 (B-part of the AB-system, J=12.0 Hz; 1H, CH$_2$-Ph), 4.85 (dd, J$_{4,3}$=1.0 Hz, J$_{4,5}$=10.0 Hz; 1H, 4-H), 5.01 (t, J$_{1',2'}$=5,5 Hz; 1H, 1'-H), 5.33 (s; 1H, 1-H), 7.24-7.40 (m; 5H, Ph-H).

$^{13}$C-NMR (50 MHz, CDCl$_3$): 1 Diastereomer: δ=15.28 (C-2''), 20.57, 20.76 (OAc), 35.72 (C-2'), 49.20, 53.18 (C-2, C-3), 62.90, 63.14 (C-6, C-1''), 62.97, 65.04 (C-4, C-5), 65.91 (C-3'), 73.00 (CH$_2$-Ph), 91.47 (C-1), 99.20 (C-1'), 127.48, 127.53, 128.22 (C-2, C-3, C-4, arom), 138.06 (C-1, arom.), 169.33, 170.47 (C=O)

MS (200 eV, DCI, NH$_3$): m/e=456 (100%, M+NH$_4^-$)

C$_{22}$H$_{30}$O$_9$ (438.5) Calc.: C 60.26 H 6.90 Found: C 60.17 H 7.00

EXAMPLE 10

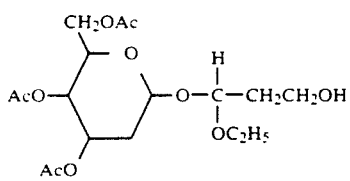

(1'RS)-1'-Ethoxy-3'-hydroxy-propyl-3,4,6-tri-O-acetyl-2-desoxy-α-D-arabino-hexopyranoside 500 mg of the compound from Example 1 (1.04 mmol) were reacted according to GWP4. The period of the reaction was 0.5 hours. Column chromatography after working up on 30 g of silica gel (LS 1c) produced 393 mg (96%) of a colorless oil. $R_F$=0.10 (LS 1a).

$[\alpha]_D^{20}$=+102° (c=1, CHCl$_3$). (1R,1'R)=I; (1R,1'S)=II.

IR (Film): 3500 (O—H), 2990 (C—H), 1740 (C=O), 1370 (C—H), 1230 (C—O), 1130, 1040, 970 cm$^{-1}$ $^1$H-NMR (200 MHz, CDCl$_3$): δ1.21 (t, J$_{2'',1'''}$=7.0 Hz; 0.75H, 2''-H$_3$, II), 1.43 (t, J$_{2'',1''}$=J$_{2'',1'''}$=7.0 Hz; 2.25H, 2''-H$_3$, I), 1.82-2.12 (m; 4H, 2-H$_a$, OH), 2.03, 2.05, 2.09 (3xs; 9H, OAc), 2.21 (ddd, J$_{2e,1}$=1,5 Hz, J$_{2e,2a}$=13.0 Hz, J$_{2e,3}$=5.5 Hz; 0.25H, 2-H$_e$, II), 2.30 (ddd, J$_{2e,1}$=1.5 Hz, J$_{2e,2a}$=13.0 Hz, J$_{2e,3}$=5.5 Hz; 0.75H, 2-H$_e$, I), 3.43-3.94 (m; 4H, 1'''-H, 3'-H$_2$), 3.98-4.14 (m; 1.75H, 6-H, I+II, 5-H, I), 4.13-4.23 (m; 0.25H, 5-H, II), 4.28 (dd, J$_{6',5}$=5,5 Hz, J$_{6',6}$=12.5 Hz; 0.75H, 6'-H, I), 4.32 (dd, J$_{6',5}$=4,5 Hz, J$_{6',6}$=12.0 Hz; 0.25H, 6'-H, II), 3.86 (dd, J$_{1',2'}$=5.0 Hz, J$_{1',2}$=7.0 Hz; 0.25H, 1'-H, II), 4.93 (t, J$_{1',2'}$=5.0 Hz, J$_{1',2'}$=7.0H; 0.25H, 1'-H. II), 4.93 (t, J$_{1',2'}$=5.5 Hz; 0.75H, 1'-H, I), 5.00 (t, J$_{4,3}$=J$_{4,5}$=10.0 Hz; 0.75H, 4-H, I), 5.04 (t, J$_{4,3}$=J$_{4,5}$=10.0 Hz; 0.25H; 4-H, II), 5.29-5.33 (m; 1H, 1-H), 5.34 (ddd, J$_{3,2e}$=5.5 Hz, J$_{3,2a}$=11.5 Hz, J$_{3,4}$=10.0 Hz; 0.75H, 3-H, I), 5.36

(ddd, $J_{3,2e}=5.5$ Hz, $J_{3,2a}=11.5$ Hz, $J_{3,4}=10.0$ Hz; 0.25H, 3-H, II)

$^{13}$C-NMR (50.3 MHz, CDCl$_3$): δ=14.68 (C-1″, II), 14.76 (C-2″, I), 20.1, 20.33 (OAc), 34.31, 36.50 (C-2, C-2′, I), 35.10, 36.84 (C-2, C-2′, II), 57.77 (C-3′, I), 57.88 (C-3′, II), 61.81, 61.98 (C-6), C-1″, I), 63.19 (C-1″, II), 67.85, 68.03, 68.45, 68.97 (C-3, C-4, C-5), 93.00 (C-1), 98.50 (C-1′, I), 101.54 (C-1′, II), 169.37, 169.59, 170.16 (C=O).

MS (70 eV): m/e=273 (6%, M− aglycone), 214 (3%, M+ H-aglycone-HOAc), 213 (29%, M-aglycone-HOAc), 153 (22%, M-aglycone-2xHOAc), 111 (22%, M-aglycone-2xHOAc-ketene), 103 (95%, CH(OC$_2$H$_5$)CH$_2$CH$_2$OH), 59 (53%), 45 (52%), 43 (100%, CH$_3$CO)

C$_{17}$H$_{28}$O$_{10}$ (392.4) Calc.: C 52.04 H 7.19 Found: C 51.87 H 7.21

EXAMPLE 11

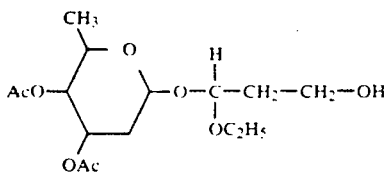

(1′RS)-1′-Ethoxy-3′-hydroxy-propyl-3,4-di-O-acetyl-2,6-didesoxy-α-L-arabino-hexopyranoside 800 mg of the compound from Example 7 (1.89 mmol) were reacted for 20 minutes according to GWP4. Subsequent chromatography on 20 g of silica gel (LS 1a) gave 613 mg (97%) of a colorless oil. R$_F$=0.37 (LS 1a) $[\alpha]_D^{20}$=−121.3° (c=1, CHCl$_3$), (1S,1′S)=I, (1S,1′R)=II.

IR (Film): 3500 (O—H), 2990, 2940 (C—H), 2880 (C—H), 1740 (C=O), 1370 (C—H), 1250, 1230 (C—O), 1140, 1050, 980 cm$^{-1}$ $^1$H-NMR (200 MHz, CDCl$_3$): δ=1.17 (d, J$_{6,5}$=6.0 Hz; 3H, 6-H$_3$), 1.22 (t, J$_{2″,1″}$=7.0 Hz; 3H, 2″-H$_3$), 1.84 (ddd, J$_{2a,1}$=4.0 Hz, J$_{2a,2e}$=13.0 Hz, J$_{2a,e}$=11.5 Hz; 1H, 2-H$_a$), 1.86-2.08 (m; 2H, 2′-H$_2$), 2.01, 2.05 (2sx; 6H, OAc), 2.19 (ddd, J$_{2e,1}$=1.5 Hz, J$_{2e,2a}$=13.0 Hz, J$_{2e,3}$=5.5 Hz; 0.25H, 2-H$_e$, II), 2.27 (ddd, J$_{2e,1}$=1.5 Hz, J$_{2e,2a}$=13.0 Hz, J$_{2e,3}$=5.5 Hz; 0.75H, 2-H$_e$, I), 3.51 (dq, J$_{1″,2}$=7.0 Hz, J$_{1″,1″}$=9.5 Hz, 1H, 1″-H), 3.70 (dq, J$_{1″,2″}$=7.0 Hz, J$_{1″,1″}$=9.5 Hz; 1H, 1″-H), 3.68-3.87 (m; 2H, 3′-H$_2$), 3.87 (dq, J$_{5,6}$=6.0 Hz, J$_{5,4}$=9,5 Hz; 0.75H, 5-H, I), 4.03 (dq, J$_{5,6}$=6,0 Hz, J$_{5,4}$=9.5 Hz; 0.25H, 5-H, II), 4.7 (t, J$_{4,5}$=J$_{4,3}$=9.5 Hz; 0.75H, 4-H, I), 4.76 (t, J$_{4,5}$=J$_{4,3}$=9.5 Hz; 0.25H, 4-H, II), 4.89 (t, J$_{1′,2′}$=5.5 Hz, 1H, 1′-H), 5.16 (dd, J$_{1,2e}$=1,5 Hz, J$_{1,2a}$=4.0 Hz; 0.25H, 1-H, II), 5.20 (dd, J$_{1,2e}$=1.5 Hz, J$_{1,2a}$=4.0 Hz; 0.75H, 1-H, I), 5.25 (ddd, J$_{3,2e}$=5.5 Hz, J$_{3,2a}$=11.5 Hz, J$_{3,4}$=9.5 Hz; 1H, 3-H)

$^{13}$C-NMR (50.3 MHz, CDCl$_3$): δ=15.21 (C-2″, II), 15.27 (C-2″, I), 17.51 (C-6, I), 17.55 (C-6, II), 20.80, 20.95 (OAc), 35.05, 35.98 (C-2, C-2′, I), 35.73, 37.11 (C-2, C-2′, II), 58.54 (C-3′, I), 58.63 (C-3′, II), 62.47 (C-1″, I), 63,60 (C-1″, II), 66.16, 68.89 (C-3, C-5, I), 66.28, 69.03 (C-3, C-5, II), 74.60 (C-4), 93.49 (C-1, II), 93.61 (C-1, I), 99.40 (C-1′, I), 102.05 (C-1′, II), 170.06, 170.13 (C=O)

MS (200 eV, DCI, NH$_3$): m/e=352 (100%, M+NH$_4^+$)

C$_{15}$H$_{26}$O$_8$ (334.4) Calc.: C 53.88 H 7.84 Found: C 53.83 H 7.93

EXAMPLE 12

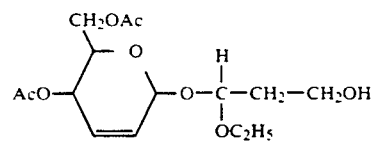

(1′RS)-1′-Ethoxy-3′-hydroxy-4,6-di-O-acetyl-2,3-didesoxy-D-erythro-hex-2-enopyranoside 680 mg of (1′RS)-1′-ethoxy-3′-(4-methoxyphenyl)-methoxy-propyl-4,6-di-O-acetyl-2,3-di-desoxy-D-erythro-hex-2-enopyranoside (1.51 mmol) are dissolved in a suspension of 90 ml of dichloromethane and 5 ml of water. 451 mg of 2,3-dichloro-5,6-dicyano-p-benzoquinone (1.99 mmol) are added at room temperature. The reaction mixture is colored green and changes its colour to yellow during the 4 hour and 15 minute reaction time. The clear emulsion at the beginning is made turbid by precipitated hydroquinone. After completion of the reaction (TLC checking), 50 ml of a buffer (pH 7) are added. After separating off the dichloromethane, the black aqueous phase is extracted twice using dichloromethane. After drying and removing the solvent, the residue is purified as rapidly as possible by column chromatography on 22 g of silica gel (LS 1c), since otherwise the resulting hydroquinone cleaves the glycoside. 422 g (84%) of a colourless oil are obtained. $[\alpha]_D^{20}$=+115.8° (c=0.5, CHCl$_3$). Diastereomer ratio: (1R,1′R):(1R,1′S)=I:II=60:40.

IR (Film): 3500 (O—H), 2980, 2930, 2890 (C—H), 1740 (C=O), 1370 (C—H), 1240 (C—O), 1130, 1000, 960 cm$^{-1}$ $^1$H-NMR (200 MHz, CDCl$_3$); δ=1.24 (t, J$_{2″,1″}$=7.0 Hz; 1.8H, 2″-H$_3$, I), 1.25 (t, J$_{2″,1″}$=7,0 Hz, 1.2H, 2″-H$_3$, II), 1.97 (q(br), J$_{2′,1′}$=J$_{2′,3′}$=6.0 Hz; 2H, 2′-H$_2$), 1.90-2.05 (m; 1H, OH, D$_2$O-exchange), 2.10 (s(br); 6H, OAc), 3.46-3.99 (m; 4H, 3′-H$_2$, 1″-H$_2$), 4.02-4.28 (m; 3H, 5-H, 6-H$_2$), 4.92 (t, J$_{1′,2′}$=5.5 Hz; 0,4H, 1′-H, II), 5.02 (t, J$_{1′,2′}$=5.5 Hz; 0.6H, 1′-H, I), 5.24-5.48 (m; 2H, 1-H, 4-H), 5.73-5.98 (m; 2H, 2-H, 3-H)

$^{13}$C-NMR (50 MHz, CDCl$_3$): δ=15.19 (C-2″, II), 15.30 (C-2″, I), 20.73, 20.78, 20.97 (OAc), 36.99 (C-2′, II), 37.16 (C-2′, I), 58.73 (C-1″, I), 58.85 (C-1″, II), 62.79, 63.11, 63.16, 63.80 (C-6, C-3′), 65.01, 67.48 (C- 4, C-5, II), 65.22, 67.32 (C-4, C-5, I), 90.30, (C-1, II), 91.91 (C-1, I), 101.25 (C-1′, I), 102.34 (C-1′, II), 127.25, 129.46 (C-2, C-3, I), 127.71, 129.14 (C-2, C-3, II), 170.25, 170.74 (C=O) MS (200 eV, DCI, NH$_3$): m/e=350 (100%, M+NH$_4^+$)

C$_{15}$H$_{24}$O$_8$ (332.4) Calc.: C 54.21 H 7.28 Found: C 53.81 H 7.57

EXAMPLE 13

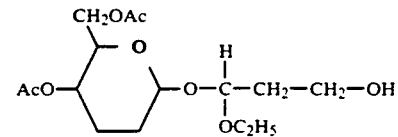

(1'RS)-1'-Ethoxy-3'-hydroxy-propyl-4,6-di-O-acetyl-2,3-di-desoxy-α-D-erythro-hexopyranoside 300 mg of (1'RS)-1'-ethoxy-3'-phenyl-methoxypropyl-4,6-di-O-acetyl-2,3-didesoxy-D-erythro-hex-2-enopyranoside (Example 8) (0.71 mmol) were reacted according to GWP4. After 30 minutes, the mixture was worked up and chromatographed on 20 g of silica gel (LS 1d). 196 mg (83%) of a colorless oil were obtained. $R_F = 0.16$ (LS 1a) $[\alpha]_D^{20} = +116.4°$ (c=1, CHCl₃), diastereomer ratio: (1R,1'R):(1R,1'S) = I:II = 60:40.

IR (Film): 3500 (O—H), 2980 (C—H), 2900 (C—H), 1750 (C=O), 1370 (C—H), 1240 (C—O), 1130, 1040, 980 cm⁻¹

¹H-NMR (200 MHz, CDCl₃): δ = 1.22 (t, $J_{2'',1''} = 7.0$ Hz; 1.8H, 2''-H₃, I), 1.24 (t, $J_{2'',1''} = 7.0$ Hz; 1.2H, 2''-H₃, II), 1.78-2.02 (m; 4H, 2-H₂, 3-H₂), 2.06, 2.10 (2xs, 6H, OAc), 2.38 (s(br); 1H, OH, D₂O-exchange), 3.52 (dq; $J_{1'',2''} = 7.0$ Hz, $J_{1'',1'''} = 9.5$ Hz; 0.4H, 1''-H, II), 3.55 (dq, $J_{1'',2''} = 7.0$ Hz, $J_{1'',1'''} = 9.5$ Hz; 0.6H, 1''-H, I), 3.64-3.92 (m; 3H, 1'''-H, 3'-H₂), 3.92-4.32 (m; 3H, 6-H₂, 5-H), 4.66-4.82 (m; 1H, 4-H), 4.87 (dd, $J_{1',2} = 6.0$ Hz, $J_{1',2} = 4.5$ Hz; 0.4H, 1'-H, II), 4.95 (t, $J_{1,2} = 5.5$ Hz; 0.6H, 1'-H, I), 5.01 (s(br); 0.4H, 1-H, II), 5.16 (s(br); 0.6H, 1-H, I)

¹³C-NMR: (50 MHz, CDCl₃): δ = 15.26 (C-2'', II), 15.29 (C-2'', I), 20.77, 21.06 (OAc), 27.76 (C-3, II), 23.94 (C-3, I), 28.52 (C-2, I), 29.24 (C-2, II), 37.14 (C-2'), 58.62 (C-3', I), 58.71 (C-3', II), 62.87, 63.28, 63.91 (C-6, C-1'''), 67.78, 69.33 (C-4, C-5, II), 67.83, 69.22 (C-4, C-5, I), 93.09 (C-1, II), 93.70 (C-1, I), 99.93 (C-1', I), 102.20 (C-1', II), 170.05, 170.91 (C=O)

MS (70 eV): m/e=216 (5%, M+H⁺-aglycone), 215 (47%, M-aglycone), 155 (11%, M-aglycone-HOAc), 103 (100%, CH(OC₂H₅)CH₂CH₂OH), 95 (16%), 75 (37%, HO—CH—CH₂—CH₂—OH), 43 (91%, CH₃CO)

C₁₅H₂₆O₈ (334.4) Calc.: C 53.88 H 7.84 Found: C 54.03 H 7.92

EXAMPLE 14

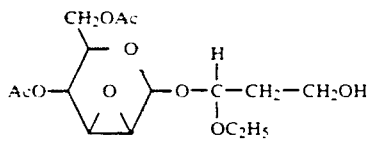

(1'RS)-1'-Ethoxy-3'-hydroxy-propyl-4,6-di-O-acetyl-2,3-anhydro-α-D-mannopyranoside 619 mg of (1'RS)-1'-ethoxy-3'-phenylmethoxypropyl-4,6-di-O-acetyl-2,3-anhydro-α-D-mannopyranoside (Example 9) (1.41 mmol) were reacted according to GWP4. After 0.5 hours, the mixture was worked up and chromatographed on 10 g of silica gel (LS 1a). 422 mg (86%) of a colorless oil were obtained. $R_F$ 0.19 (LS 1a) $[\alpha]_D^{20} = 94.8°$ (c=1, CHCl₃), (1R,1'R):(1R,1'S) = I:II = 60:40.

IR (Film): 3500 (O—H), 2980, 2940 (C—H), 1740 (C=O), 1370 (C—H), 1230 (C—O), 1130, 1040, 970 cm⁻¹

¹H-NMR (200 MHz, CDCl₃): δ = 1.26 (t, $J_{2'',1''} = 7.0$ Hz; 3H, 2''-H₃), 1.93-2.05 (mc; 2H, 2'-H₂), 2.07, 2.08, 2.13 (3xs; 6H, OAc), 2.23 (s(br); 1H, OH, D₂O- exchange), 3.07 (dd, $J_{3,2} = 3.5$ Hz, $J_{3,4} = 1.0$ Hz; 0.4H, 3-H, II), 3.16 (dd, $J_{3,2} = 3.5$ Hz, $J_{3,4} = 1.0$ Hz; 0.6H, 3-H, I), 3.26 (d, $J_{2,3} = 3.5$ Hz; 1H, 2-H), 3.57, 3.59 (2xdq, $J_{1'',2''} = 7.0$ Hz, $J_{1'',1'''} = 9.5$ Hz; 1H, 1''-H), 3.69-4.20 (m; 6-H₂, 5-H, 3'-H₂, 1'''-H), 4.84 (dd, $J_{4,3} = 1.0$ Hz, $J_{4,5} = 10.0$ Hz; 0.6H, 4-H, I), 4.88 (dd, $J_{4,3} = 1.0$ Hz, $J_{4,5} = 10.0$ Hz; 1H, 4-H, II), 4.96 (dd, $J_{1',2'} = 6.0$ Hz, $J_{1',2'} = 5.0$ Hz; 0.4H, 1'-H, II), 5.03 (t, $J_{1',2'} = 5.0$ Hz; 0.6H, 1'-H, I), 5.30 (s; 0.4H, 1-H, II), 5.34 (s; 0.6H, 1-H, I)

¹³C-NMR (50 MHz; CDCl₃): δ = 15.16 (C-2'', II), 15.28 (C-2'', I), 20.66, 20.70, 20.79 (OAc), 37.14 (C-2'), 48.11, 53.28 (C-2, C-3, I), 49.38, 53.11 (C-2, C-3, II), 58.43 (C-3', I), 58.55 (C-3', II), 62.85, 65.13 (C-4, C-5, I), 63.09, 65.22 (C-4, C-5, II), 63.14, 64.11 (C-6, C-1'''), 90.82 (C-1, II), 92.12 (C-1, I), 100.63 (C-1', I), 102.43 (C-1', II), 169.46, 170.51, 170.56 (C=O)

MS (200 eV, DCI, NH₃): m/e=366 (100%, M+NH₄⁺)

C₁₅H₂₄O₉ (348.4) Calc.: C 51.72 H 6.94 Found: C 51.53 H 7.04

EXAMPLE 15

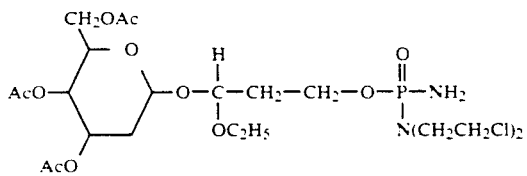

(3'RS)-1'-O-(3'-Ethoxy-3'-(3,4,6-tri-O-acetyl-2-desoxy-α-D-arabino-hexopyranosyloxy))-propyl-N,N-bis-(2-chloroethyl)-phosphorodiamidate 370 mg of the compound from Example 10 (0.94 mmol) were reacted with N,N-bis-(2-chloroethyl)-dichlorophosphoramide according to GWP5. After 48 hours, the educt had reduced quantitatively. $R_F = 0.30$ (LS 1) (intermediate). Ammonia was introduced for 3 hours. Chromatography on 30 g of silica gel (LS 3b) produced 235 mg (42%) of a colorless oil. $R_F = 0.30$ (LS 3b). $[\alpha]_D^{20} = +62.4°$ (c=1, CHCl₃). The diastereomer ratio was 1:1:3:3.

IR (Film): 3700-3100 (O—H, N—H), 2980, 2900 (C—H), 1740 (C=O), 1370 (C—H), 1240 (C—O), 1140, 1100 (P—N), 1040, 980, 740 cm⁻¹ (C—Cl)

¹H-NMR (200 MHz, CDCl₃): δ = 1.21 (t, $J_{2''',1'''} = 7.0$ Hz; 3H, 2'''-H₃), 1.76-2.08 (m; 3H, 2''-H$_a$, 2'-H₂), 2.03, 2.06, 2.10 (3xs; 9H, OAc), 2.18-2.34 (m; 1H, 2''-H$_e$), 2.78-2.96 (m; 2H, NH₂(D₂O- exchange)), 3.36-3.84 (m; 10H, 1'''-H₂, 2×N—CH₂—CH₂), 3.96-4.24 (m; 4H, 6''-H, 5''-H, 3'-H₂), 4.31 (2xdd, $J_{6''',5''} = 5.0$ Hz, $J_{6''',6''} = 11.5$ Hz; 1H, 6'''-H), 4.79, 4.80, 4.85, 5.86 (4xt, $J_{3',2'} = 5.5$ Hz; 1H, 3'-H), 5.02, 5.04 (2xt, $J_{4,3} = J_{4,5} = 10.0$ Hz; 1H, 4''-H), 5.24-5.30 (m; 2H, 1''-H, 3''-H)

C₂₁H₃₇Cl₂N₂O₁₁P (595,4) Calc.: C 42,46 H 6.26 Found: C 42.54 H 6.43

EXAMPLE 16

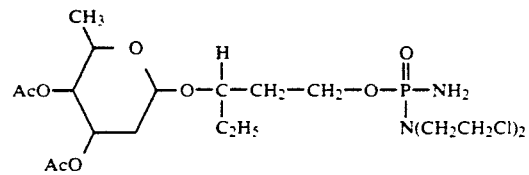

(3'RS)-1'-O-(3'-Ethoxy-3'-(3,4-di-O-acetyl-2,6-dideoxy-α-L-arabino-hexopyranosyloxy))-propyl-N,N-bis-(2-chloroethyl)-phosphorodiamidate 367 mg of the compound from Example 11 (1.10 mmol) were reacted with N,N-bis-(2-chloroethyl)-dichlorophosphoramide according to GWP5. The conversion was complete after 24 hours. $R_F=0.50$ (LS 1) (intermediate). Ammonia was then introduced for 5 h. Chromatography on 40 g of silica gel (LS 5a) gave 314 mg (53%) of product. $R_F=0.42$ (LS 5a). $[\alpha]_D^{20}=-79.7°$ (c=1, CHCl$_3$). Diastereomer ratio=1:1.5:4.5:5.

IR (KBr): 3650-3100 (NH), 2980 (C—H), 1740, 1730 (C=O), 1370 (C—H), 1260, 1240 (P=O, C—O), 1140, 1040, 980 cm$^{-1}$.

$^1$H-NMR (200 MHz, CDCl$_3$): δ=1.17, 1.19 (2xd, $J_{6'',5''}=6.0$ Hz; 3H, 6''-H$_3$), 1.21 (t, $J_{2''',1'''}=7.0$ Hz; 3H, 2'''-H$_3$), 1.70-194 (m; 1H, 2''-H$_a$), 1.95-2.10 (m; 2H, 2'-H$_2$), 2.01, 2.05 (2xs; 6H, OAc), 2.15-2.31 (mc; 1H, 2''-H$_c$), 2.80-2.94 (m; 2H, NH$_2$, D$_2$O- exchange), 3.36-3.78 (m; 10H, 1'''-H, 1''''-H, 2×CH$_2$—N, 2×CH$_2$—Cl), 3.78-4.25 (m; 3H, 5''-H, 1'-H$_2$), 4.75, 4.76 (2xt, $J_{4'',3''}=9.5$ Hz; 1H, 4''-H), 4.85, 4.86 (2xt, $J_{3',2'}=5.0$ Hz, $J_{3',2''}=5.5$ Hz; 1H, 3'-H), 5.13-5.23 (m; 1H, 1''-H), 5.17-5.34 (m; 1H, 3'''-H)

$^{13}$C-NMR (50.3 MHz, CDCl$_3$): δ=15.21, 15.28 (C-2'''), 17.59 (C-6''), 20.86, 21.01 (OAc), 35.02, 35.17, 35.25, 35.30, 25.39, 35.61, 35.68, 35.73 (C-2'', C-2'), 42.51 (CH$_2$—Cl), 49.28 (d, $J_{P,N,C}=4.9$ Hz; CH$_2$—N), 61.28, 61.37, 61.46, 61.55, 62.13, 62.17, 63.38, 63.57 (C-1''', C-1'), 66.30, 66.41, 66.44, 68.84, 69.05 (C-3'', C-5''), 74.54, 74.60 (C-4''), 93.36, 93.72, 93.80 (C-1''), 97.56, 97.63, 100.45, 100.73 (C-1'), 170.15, 170.21, 170.28, 170.32 (C=O)

MS (200 eV, DCI, NH$_3$): m/e=556, 554 (88%, 100%, M+NH$_4^-$), 307, 305 (19%, 56%, aglycone$^-$)

C$_{19}$H$_{35}$Cl$_2$N$_2$O$_9$P (537.4) Calc.: C 42.47 H 6.57
Found: C 42.52 H 6.43

EXAMPLE 17

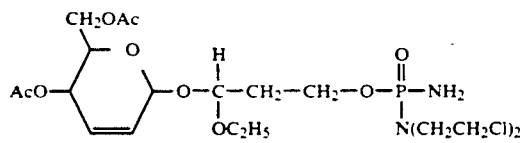

(3'RS)-1'-O-(3'-Ethoxy-3'-(4,6-di-O-acetyl-2,3-didesoxy-D-erythro-hex-2-enopyranosyloxy))-propyl-N,N-bis-(2-chloroethyl)-phosphorodiamidate 300 mg of the compound from Example 12 (0.90 mmol) were reacted at room temperature with N,N-bis-(2-chloroethyl)-dichlorophosphoramide according to GWP5. The conversion was complete after 72 hours. $R_F=0.43$ (LS 1a) (intermediate). Ammonia was introduced for 4 h. Chromatography on 20 g of silica gel (LS 3b) gave 278 mg (58%) of product. $R_F=0.24$ (LS 3b). $[\alpha]_D^{20}=+69.4$ (c=0.5, CHCl$_3$).

The diastereomer ratio was: (1RS, 3'R,1''R):(1RS, 3'S,1''R)=I:II=(2.5:2.5):(1:1).

IR (Film): 3400, 3240, 3100 (O—H, N—H), 2980, 2940, 2900 (C—H), 1740 (C=O), 1570, 1370 (C—H), 1230 (C—O), 1140, 1100, 1040, 980, 750 cm$^{-1}$ (C—Cl)

$^1$H-NMR (200 MHz, CDCl$_3$): δ=1.23 (t(br), $J_{2''',1'''}=7.0$ Hz; 3H, 2'''-H$_3$), 1.95-2.10 (m; 2H, 2'-H$_2$), 2.09, 2.11 (2xs, 6H, OAc), 2.50-2.90 (s(br); 2H, NH$_2$ (D$_2$O-exchange)), 3.36-3.88 (m; 10H, 1'''-H$_2$, N—CH$_2$, CH$_2$—Cl), 3.98-4.35 (m; 5H, 1'-H$_2$, 5''-H, 6''-H$_2$), 4.86, 4.87 (2xt, $J_{3',2'}=5.5$ Hz; 0.3H, 3'-H, II), 4.96, 4.97 (2xt, $J_{3',2'}=5.5$ Hz; 0.7H, 3'-H, I), 5.25-5.48 (m; 2H, 1''-H, 4''-H), 5.74-6.01 (m; 2H, 2''-H, 3''-H)

$^{13}$C-NMR (50 MHz, CDCl$_3$): δ=15.15 (C-2''', II), 15.26 (C-2''', I), 20.79, 20.95 (OAc), 35.75, 35.89 (C-2'), 42.50 (C—Cl), 49.21, 49.30, 49.37 (C—N), 61.41, 61.51, 61.61, 61.70, 62.30, 62.51, 62.74, 62.88, 63.05, 63.56 (C-1''', C-6'', C-1'), 64.96, 67.42 (C-4'', C-5'', II), 66.12, 67.14 (C-4'', C-5'', I), 90.09, 90.25 (C-1'', II), 91.61, 91.79, (C-1'', I), 99.13 (C-3', I), 100.28, 100.32 (C-3', II), 127.10, 127.18, 129.28, 129.39 (C-2'', C-3'', I), 127.67, 128.90, 128.93 (C-2'', C-3'', II), 170.05, 170.55, 170.63 (C=O)

MS (200 eV, DCI NH$_3$): m/e=554, 552 (18%, 26%, M+NH$_4^-$), 248 (100%), 161, 159 (62%, 95%)

C$_{19}$H$_{33}$Cl$_2$N$_2$O$_9$P (535.4) Calc.: C 42.63 H 6.21
Found: C 43.02 H 6.39

EXAMPLE 18

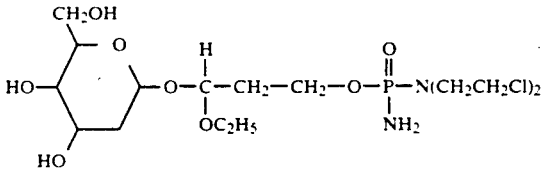

Example 18 can be prepared from Example 15 according to working procedure 6 (GWP6).

EXAMPLE 19

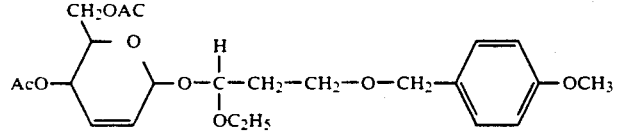

(1'RS)-1'-Ethoxy-3'-(4-methoxyphenyl)-methoxypropyl-4,6-di-O-acetyl-2,3-di-desoxy-D-erythro-hex-2-enopyranoside 300 mg (0.99 mmol) of Example 4 were reacted with 1,2-diethoxy-3-(4-methoxyphenyl)-methoxypropane (A) and 3-(4-methoxyphenyl)-methoxy-propanal (B) in dichloromethane at −90° C. according to GWP2. After 24 hours, half the amount of A, B and trimethylsilyl triglate was added using a syringe. After 30 hours, the mixture was worked up and chromatographed on 40 g of silica gel. 368 mg (82%) of a colorless oil were obtained. $R_F=0.24$ (LS 2e). $[\alpha]_D^{20}=+88°$ (c=0.5, CHCl$_3$). Diastereomer ratio: (1R,1'R):(1R,1'S)=I:II=60:40.

IR (Film): 2980, 2940, 2900 (C—H), 1740 (C=O), 1615, 1515 (C=C), 1370 (C—H), 1240 (C—O), 1100, 1040, 820 cm$^{-1}$ $^1$H-NMR (200 MHz, CDCl$_3$): δ=1.20 (t, J$_{2'',1''}$=7.0 Hz; 3H, 2''-H$_3$, I), 1.90-2.11 (m; 2H, 2'-H$_2$), 2.04, 2.07, 2.08, 2.09 (4xs; 6H, OAc), 3.41-3.87 (m; 4H, 1''-H$_2$, 3'-H$_2$), 3.80 (s; 3H, OCH$_3$), 4.00-4.30 (m; 3H, 5-H, 6-H$_2$), 4.42 (s(br); 2H, PhCH$_2$O), 4.88 (t, J$_{1',2'}$=5.5 Hz; 0.4H, 1'-H, II), 4.98 (t, J$_{1',2'}$=5.5 Hz; 0.6H, 1'-H, I), 5.16-5.36 (m; 2H, 1-H, 4-H), 5.64-5.99 (m; 2H, 2-H, 3-H), 6.82-6.91 (m; 2H, Ph—H), 7.19-729 (m; 2H, Ph—H)

$^{13}$C-NMR (50 MHz, CDCl$_3$): δ=15.14 (C-2'', II), 15.30 (C-2'', I), 20.57, 20.65, 20.83 (OAc), 35.14 (C-2', I), 35.47 (C-2', II), 55.08 (OCH$_3$), 62.33, 62.88, 65.75 (C-6, C-3', C-1''), 63.05, 63.48, 65.58 (C-6, C-3', C-1'', II), 64.97, 67.27 (C-4, C-5, II), 65.15, 67.12 (C-4, C-5, I), 72.54 (PhCH$_2$O), 90.42 (C-1, II), 91.03 (C-1, I), 99.30 (C-1', I), 101.30 (C-1', II), 113.59 (C-2 arom., C-6 arom., C-6 arom.), 127.47, 127.58, 127.92, 128.55, 128.99, 129.10, 129.16, 129.33 (C-2, C-3, C-3 arom., C-5 arom.), 130.22, 130.29, 130.40, 130.40, 130.45 (C-4 arom.), 159.00, 159.05 (C-1 arom.), 169.90, 170.34, 170.40 (C=O)

MS (200 eV, DCI, NH$_3$): m/e=470 (100%, M—NH$_4^+$)

C$_{23}$H$_{32}$O$_9$ (452.5) Calc.: C 61.05 H 7.13 Found: C 60.69 H 7.04

EXAMPLE 20

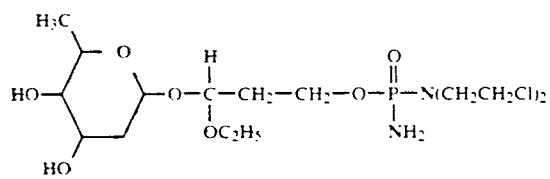

Example 20 can be prepared from Example 16 according to working procedure 6 (GWP6).

EXAMPLE 21

(3'-RS)-1'-O-(3'-Ethoxy-3'-(2,3-di-desoxy-D-erythro-hex-2-enopyranoxyl-oxy)-propyl-N,N-bis-(2-chloroethyl)-phosphorodiamidate

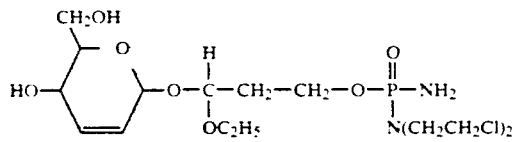

Example 21 can be prepared from Example 17 according to working procedure 6 (GWP6).

It will be appreciated that the instant specification and claims are set forth by way of illustration and not limitation, and that various modifications and changes may be made without departing from the spirit and scope of the present invention.

What is claimed is:

1. A compound selected from the group consisting of (I)

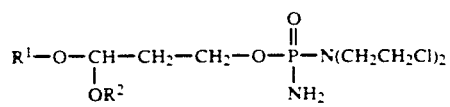

-continued

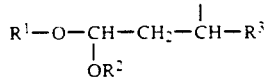
(II)

and

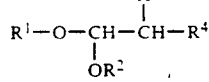
(III)

in which

R$^1$ represents saturated, unsaturated or anhydro desoxypentosyl, desoxyhexosyl or didesoxyhexosyl, where the OH moieties of the saturated, unsaturated or anhydro desoxypentosyl, desoxyhexosyl or didesoxyhexosyl are unprotected or protected, R$^2$ represents straight-chain or branched alkyl having up to ten carbon atoms, R$^3$ represents straight-chain or branched alkyl having up to ten carbon atoms, X represents halogen and R$^4$ represents straight-chain or branched alkyl having up to ten carbon atoms.

2. A compound of the formulae (I), (II) or (III) according to claim 1 in which

R$^1$ represents a radical selected from the group consisting of saturated, unsaturated or anhydro-2-desoxyhexopyranosyl, 2,6-didesoxy-hexopyranosyl, 2-desoxypentofuranosyl, 2,3-didesoxyhexenopyranosyl or 2,3-anhydropentofuranosyl, where the OH functions are unprotected or protected.

R$^2$ represents straight-chain or branched alkyl having up to 6 carbon atoms.

3. A compound of the formula (I) according to claim 1, wherein

R$^1$ represents a radical selected from the group consisting of saturated, unsaturated or anhydro-2-desoxyhexopyranosyl, 2,6-didesoxy-hexopyranosyl, 2-desoxypentofuranosyl, 2,3-didesoxyhexenopyranosyl or 2,3-anhydropentofuranosyl, which is linked glycosidically to the anomeric carbon atom, where the OH functions are unprotected or protected, and R$^2$ represents straight-chain or branched alkyl having up to 6 carbon atoms.

4. A compound of the formula (I) according to claim 1, wherein

R$^1$ represents 2-desoxy-α-D-arabino-hexo-pyranosyl, 2-desoxy-D-erythro-pento-pyranosyl, 2,6-didesoxy-α-L-arabino-hexo-pyranosyl, 2,3-anhydro-α-D-mannopyranosyl or 2,3-didesoxy-D-erythro-hex-2-enopyranosyl, where the OH moieties of the saturated, unsaturated or anhydro desoxypentosyl, desoxyhexosyl or didesoxyhexosyl are unprotected or protected and R$^2$ represents straight-chain alkyl having up to 3 carbon atoms.

5. A compound of the formula (I), according to claim 1, wherein

R$^1$ represents 2-desoxy-α-D-arabino-hexo-pyranosyl, 2,6-didesoxy-α-L-arabino-hexo-pyranosyl or 2,3-didesoxy-D-erythro-hex-2-eno-pyranosyl, where the OH functions are protected or unprotected and R$^2$ represents methyl or ethyl.

6. A compound according to claim 1, wherein the OH moieties are protected by a protecting group selected from the group consisting of methylbenzoyl, benzoyl, acetyl and benzyl.
7. A Compound according to claim 1, wherein the compound is selected from the group consisting of
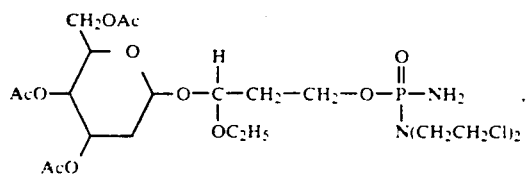
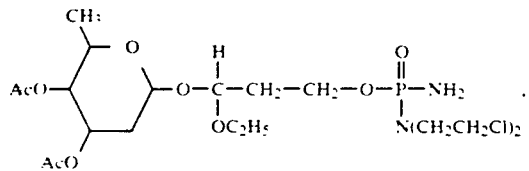
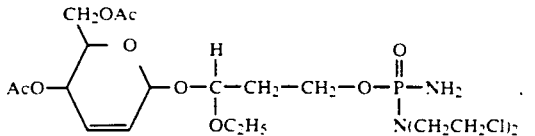
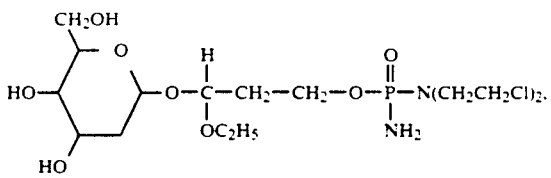
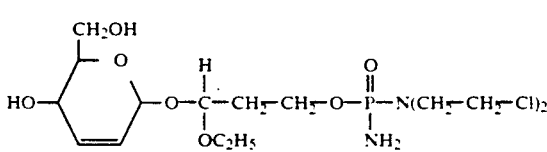
and
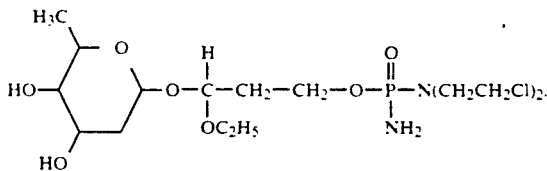
* * * * *